(12) United States Patent
Afilani

(10) Patent No.: US 11,333,627 B2
(45) Date of Patent: May 17, 2022

(54) REMOTE DETECTOR FOR DIELECTRIC MATERIAL

(71) Applicant: DKL INTERNATIONAL, INC., Fernandina Beach, FL (US)

(72) Inventor: Thomas L. Afilani, Jersey Shore, PA (US)

(73) Assignee: DKL INTERNATIONAL, INC., Fernandina Beach, FL (US)

( * ) Notice: Subject to any disclaimer, the term of this patent is extended or adjusted under 35 U.S.C. 154(b) by 225 days.

(21) Appl. No.: 16/812,701

(22) Filed: Mar. 9, 2020

(65) Prior Publication Data

US 2020/0209191 A1   Jul. 2, 2020

Related U.S. Application Data

(63) Continuation-in-part of application No. 16/797,136, filed on Feb. 21, 2020, which is a continuation-in-part of application No. 16/524,672, filed on Jul. 29, 2019.

(60) Provisional application No. 62/815,634, filed on Mar. 8, 2019, provisional application No. 62/713,233, filed on Aug. 1, 2018.

(51) Int. Cl.
   *G01N 27/60* (2006.01)
   *G01N 33/22* (2006.01)

(52) U.S. Cl.
   CPC .......... *G01N 27/60* (2013.01); *G01N 33/227* (2013.01)

(58) Field of Classification Search
   CPC .............................. G01N 27/60; G01N 33/227
   USPC ........................................................ 324/457
   See application file for complete search history.

(56) References Cited

U.S. PATENT DOCUMENTS

| 5,019,804 A | * | 5/1991 | Fraden ................... G08B 13/26 327/509 |
| 5,748,088 A | | 5/1998 | Afilani |
| 5,907,280 A | * | 5/1999 | Afilani ................... G01N 27/60 340/568.1 |
| 6,011,476 A | * | 1/2000 | Afilani ............... G08B 13/2491 340/568.1 |
| 6,078,179 A | | 6/2000 | Afilani |
| 6,346,865 B1 | | 2/2002 | Maynord et al. |
| 6,411,099 B1 | * | 6/2002 | Afilani ............... G08B 13/2491 324/452 |

(Continued)

FOREIGN PATENT DOCUMENTS

WO   WO 98/48267   10/1998

OTHER PUBLICATIONS

Senesac, Larry, and Thomas G. Thundat. "Nanosensors for trace explosive detection." materials today 11.3 (2008): 28-36. (Year: 2008).*

(Continued)

*Primary Examiner* — Christopher P McAndrew
(74) *Attorney, Agent, or Firm* — Nixon & Vanderhye P.C.

(57) ABSTRACT

A remote detector detects the presence of dielectric materials, including energetic materials. The remote detector includes a center beam secured in a pivot mount, at least one collector secured to the center beam at a proximal end via the pivot mount, and an analog matching filter coupled with the center beam via a circuit. The analog matching filter contains a replicate matching material configured to match a dipole field of a target material. In the presence of a target material, the replicate matching material causes displacement of the center beam via a dielectrokinesis (phoresis) force.

12 Claims, 9 Drawing Sheets

(56) References Cited

U.S. PATENT DOCUMENTS

| | | | |
|---|---|---|---|
| 6,496,114 | B1 | 12/2002 | Afilani |
| 6,674,366 | B1 | 1/2004 | Afilani |
| 6,686,842 | B1 | 2/2004 | Afilani |
| 10,816,456 | B2 * | 10/2020 | de Oliveira Botelho .................... G01N 21/27 |
| 2004/0114130 | A1 * | 6/2004 | Nguyen .................. G01N 1/24 356/36 |
| 2013/0228474 | A1 | 9/2013 | Sloss et al. |
| 2018/0106759 | A1 * | 4/2018 | de Oliveira Botelho .................... G01N 21/27 |

OTHER PUBLICATIONS

Wasisto, Hutomo Suryo, et al. "Airborne engineered nanoparticle mass sensor based on a silicon resonant cantilever." Sensors and Actuators B: Chemical 180 (2013): 77-89. (Year: 2013).*

* cited by examiner

REMOTE DETECTOR FOR DIELECTRIC MATERIAL

CROSS-REFERENCES TO RELATED APPLICATIONS

This application claims the benefit of U.S. Provisional Patent Application No. 62/815,634, filed Mar. 8, 2019, and this application is a continuation-in-part of U.S. patent application Ser. No. 16/797,136, filed Feb. 21, 2020, which is a continuation-in-part of U.S. patent application Ser. No. 16/524,672, filed Jul. 29, 2019, which claims the benefit of U.S. Provisional Patent Application No. 62/713,233, filed Aug. 1, 2018, the entire contents of each of which are herein incorporated by reference.

STATEMENT REGARDING FEDERALLY SPONSORED RESEARCH OR DEVELOPMENT (NOT APPLICABLE)

BACKGROUND

The present invention relates to methods and apparatus for detecting inanimate entities and, more particularly, to methods and apparatus for detecting the presence of dielectric materials including energetic materials excluding gold, silver and copper by measuring dielectrokinesis (phoresis) response.

Energetic materials are a class of material with high amount of stored chemical energy that can be released. Energetic materials include, e.g., explosives, pyrotechnic compositions, propellants (e.g., smokeless gun powders and compositions, chemicals such as diesel fuel and gasoline, etc.) combined with ammonium nitrate.

Dielectrokinesis (phoresis) (DEP) describes the force upon and mechanical behavior of initially charge-neutral matter that is dielectric polarization charged via induction by external spatially non-uniform electric fields. The severity of the spatial non-uniformity of the electric field is measured by the spatial gradient (spatial rate of change) of the electric field. A fundamental operating principle of the DEP effect is that the force (or torque) in air or other surrounding media generated at a point and space in time always points (or seeks to point) in the same direction, mainly toward the maximum gradient (non-uniformity) of the local electric field, independent of sign (+ or −) and time variations (DC or AC) of electrical fields (voltages) and of the surrounding medium dielectric properties.

The DEP force magnitude depends distinctively nonlinearly upon the dielectric polarizability of the surrounding medium, the dielectric polarizability of initially neutral matter and nonlinearly upon the neutral matter's geometry. This dependence is via the Clausius-Mossotti function, well-known from polarizability studies in solid state physics. The DEP force depends nonlinearly upon the local applied electric field produced by the target. The DEP force depends upon the spatial gradient of the square (second power) of the target's local electric field distribution at a point in space and time where a detector is located. The spatial gradient of the square of the local electric field is measured by the DEP force produced by the induced polarization charge on the detector. This constant-direction-seeking force is highly variable in magnitude both as a function of angular position (at fixed radial distance from the target) and as a function of the radial position (at a fixed angular position) and as a function of the "effective" medium polarizability. The force's detection signature is a unique pattern of the target's spatial gradient of the local electric field squared, with the detector always pointing (seeking to point) out the direction of the local maximum of the gradient pattern. All experimental results and equations of DEP are consistent with the fundamental electromagnetic laws (Maxwell's equations).

There are five known modes of dielectric polarization. These include: electronic polarization, where electron distribution about the atom nuclei is slightly distorted due to the imposed external electric field; atomic polarization, where the atoms' distributions within initially neutral matter are slightly distorted due to the imposed external electric field; nomadic polarization, where in very specific polymers, etc. highly delocalized electron or proton distributions are highly distorted over several molecular repeat units due to the imposed external electric field; rotational polarization (dipolar and orientational), where permanent dipoles ($H_2O$, NO, HF) and orientable pendant polar groups (—OH, —Cl, —CN, —$NO_2$) hung flexibly on molecules in material are rotationally aligned toward the external electric field with characteristic time constants; and interfacial (space charge) polarization, where inhomogeneous dielectric interfaces accumulate charge carriers due to differing small electrical conductivities. With the interfacial polarization, the resulting space charge accumulated to neutralize the interface charges distorts the external electric field with characteristic time constants.

The first three modes of dielectric polarization, electronic, atomic and nomadic, are molecular in distance scale and occur "instantaneously" as soon as the external electric field is imposed and contribute to the dielectric constant of the material at very high frequencies (infrared and optical). The last two polarization modes, rotational and interfacial, are molecular and macroscopic in distance scale and appear dynamically over time with characteristic time constants to help increase the high frequency dielectric constant as it evolves in time toward the dielectric constant at zero frequency. These characteristic material time constants control the dielectric and mechanical response of a material.

The modes of polarization and their dynamics in contributing to the time evolution of dielectric constants are discussed in various publications, such as H. A. Pohl, Dielectrophoresis, Cambridge University Press (1978); R. Schiller Electrons in Dielectric Media, C. Ferradini, J. Gerin (eds.), CRC Press (1991), and R. Schiller, Macroscopic Friction and Dielectric Relaxation, IEEE Transactions on Electrical Insulation, 24, 199 (1989), the well-known teachings of which are hereby incorporated by reference.

Further details with regard to DEP are described in applicant's U.S. Pat. No. 5,907,280, the contents of which are hereby incorporated by reference.

U.S. Pat. No. 6,011,476 also authored by the present applicant describes a metering circuit that detects a change in DEP effects in an environment characterized at any instant by an instantaneous ambient dielectrokinetic condition. The contents of the '476 patent are also hereby incorporated by reference.

There are numerous technologies available to identify dielectric materials with the main focus on illegal and/or dangerous materials. Examples of these materials are either in the energetic or drug category. Identification/detection is reasonably easy in a laboratory environment but becomes increasingly difficult in the field.

A first type of current technology is based on detection of trace elements of the target material (as in parts per billion). They are very sensitive to the environment and are limited in range. An example is LIDAR (light detection and ranging). LIDAR components include a laser, optics, photodetectors and software controlling the emission of laser light and to process the return light from the photodetectors. The limitation of LIDAR is that the target material or traces of the target material must be optically observable by the light emissions, and the return light from the target material must be optically received by the photodetectors.

A second type of system is generally based on the principles of radar. These systems are typically large, not portable and require a significant power source. This type does not detect the target material, but rather detects the container the material is in. An example of this is the canyon baggage check equipment at the airport.

A third type of technology is based on immunoassay binding. In immunoassay binding, a trace amount of the target material is placed on a solid support. A fluid is used to mix the first binding antibodies with the trace target material. The fluid moves the binding antibodies and the trace materials to a second location where secondary binding antibodies trap the first antibodies and the trace target material. The result is typically shown as a color change.

Another current detection technology is canines, which are trained to alert to the presence of target materials using their keen sense of smell. The use of canines is limited by the physical endurance of the canine. Also, the canine must be proximate to the target material to detect and locate the presence of the material.

BRIEF SUMMARY

The apparatus and methods of the described embodiments detect the DEP force to determine the presence of various dielectric materials including energetic materials. In the described embodiments, the DEP force is sensed in differing modes, including pressure, stress, and acceleration. The force is confirmed using multiple analytical techniques. The apparatus utilizes multiple active elements that replace the "antenna" described in the patents noted above and incorporated by reference. Moreover, active elements may include a method of amplifying the DEP force, and these active elements may be contained within an enclosure.

In an exemplary embodiment, a remote detector detects a presence of dielectric materials including energetic materials. The remote detector includes a center beam secured in a pivot mount, at least one collector secured to the center beam at a proximal end via the pivot mount, and an analog matching filter coupled with the center beam via a circuit, the analog matching filter including a replicate matching material configured to match a dipole field of a target material. The analog matching filter may include a selective permittivity that generates an opposite polarization pattern on the center beam via the circuit and thereby enables a unique electric field stored charge to be converted to a DEP force on the center beam.

The remote detector may include two collectors secured to opposite sides of the center beam. In this context, the collectors may be provided with a bend at a midpoint such that distal ends of the collectors are spaced from the center beam.

In some embodiments, the center beam may be constructed of ABS plastic. The center beam may be constructed of a combination of metal and dielectrics.

A displacement sensor may be positioned adjacent the collector. The displacement sensor may include a contact terminal or a non-contact sensor.

The detector may also include a gyroscope accelerometer coupled with the center beam and connected to the circuit.

A housing may contain the center beam, the collector and the analog matching filter.

Detection indicator lights may be coupled with the circuit, where the circuit illuminates the detection indicator lights when displacement of the center beam is detected.

BRIEF DESCRIPTION OF THE DRAWINGS

These and other aspects and advantages will be described in detail with reference to the accompanying drawings, in which.

DETAILED DESCRIPTION

Figure 1:
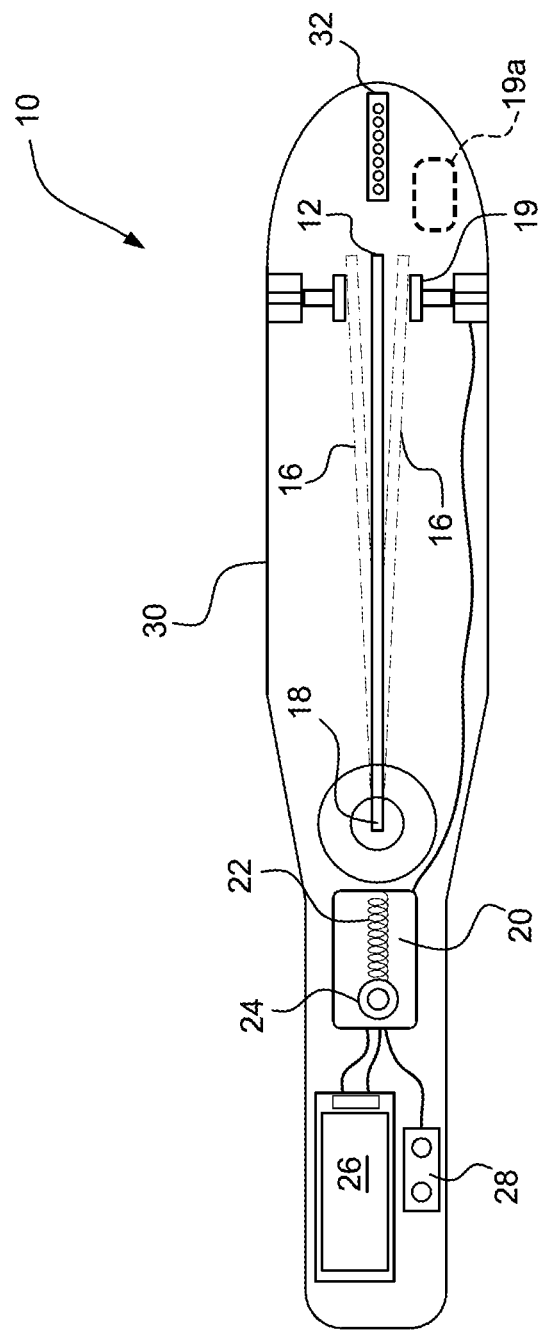
FIG. 1 is a schematic illustration of an exemplary detecting apparatus according to the described embodiments.

With reference to FIG. 1, the detecting apparatus 10 includes a center beam or cantilever 12. At least one collector 16 is secured to or in close proximity to the center beam 12 at a proximal end thereof via a pivot mount 18. In the embodiment shown in FIG. 1, two collectors 16 are secured on opposite sides of the center beam 12 via a friction fit or the like. The collectors 16 provide additional surface area for accumulating ULF charge. The accumulated charges on the collectors aid dielectrokinesis (phoresis) force.

Figure 4:
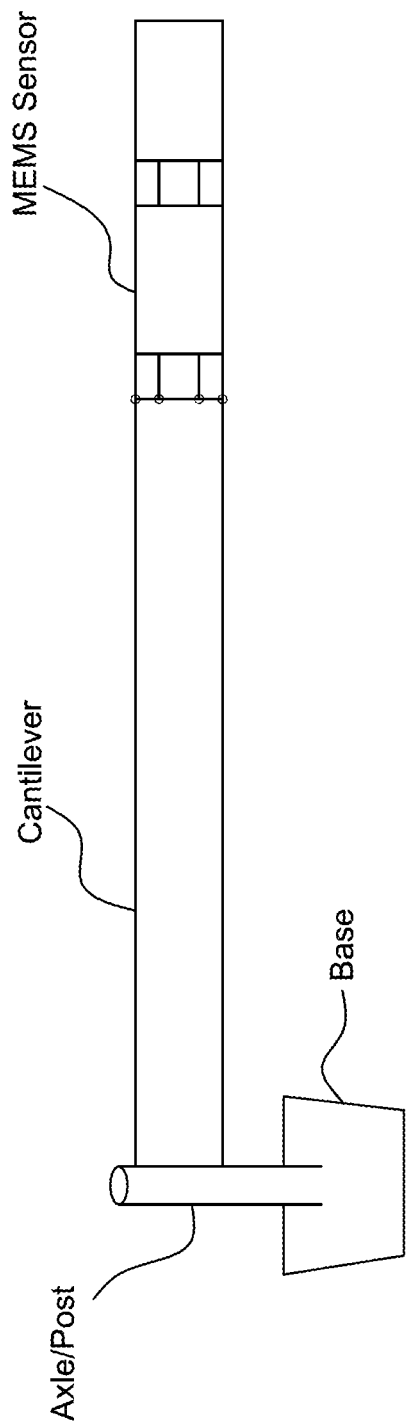
FIG. 4 shows material and dimensional variations of the center beam.
Figure 5A:
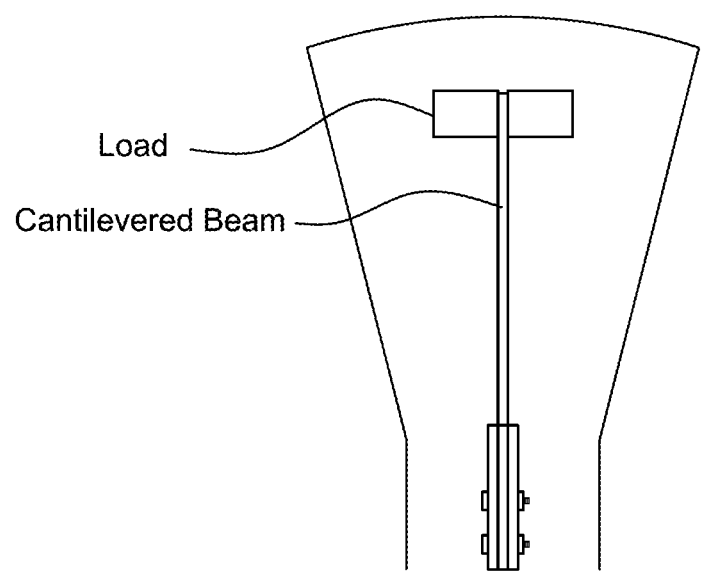
FIGS. 5(*a*) and 5(*b*) show variations in construction of the center beam.
Figure 5B:
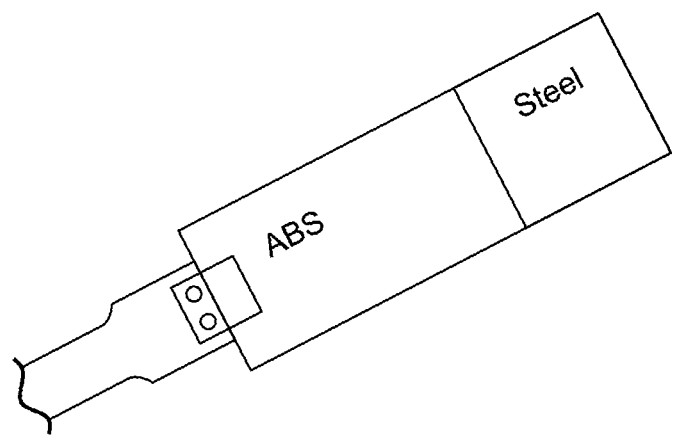

The center beam 12 is preferably constructed of acrylonitrile-butadiene-styrene (ABS) plastic or other suitable material. FIG. 4 shows material and dimensional variations of the center beam 12. Compositions of materials may be used to form the center beam 12, which may include combinations of metal and dieletrics (plastic). The center beam 12 may include MEMS or conventional sensors as part of the beam. Sensors used in the center beam 12 may detect bending forces or stress. With reference to FIGS. 5(*a*) and 5(*b*), the center beam 12 may have multiple elements that comprise beam assembly. The center beam 12 may have added weight (i.e., "load") at distal ends or elsewhere, and the center beam may be comprised of metal sections and dielectric materials such as ABS.

The collectors 16 may similarly be constructed of ABS plastic or similar material. The collectors 16 are provided with a slight bend at a midpoint such that distal ends thereof are spaced from the center beam 12. A distance between the collectors 16 and the center beam 12 at or near distal ends of the collectors 16 similarly varies by application but may be about ⅞ inch. A contact terminal 19 including a sensitivity adjustment mechanism is associated with each of the collectors 16 to detect displacement of the center beam. The contact terminals 19 are activated by physical contact with the center beam 12. The sensitivity adjustment mechanism serves to shift a position of the contact terminals 19 closer to or farther from the collectors 16. In some embodiments, non-contact sensors 19a may be utilized to detect displacement of the center beam 12. Exemplary non-contact sensors may include optical, magnetic, or other non-contact sensor devices.

Also included in the apparatus 10 are a gyroscope accelerometer 20, a tension control spring 22, a pressure switch 24, a battery 26, and an analog matching filter (AMF) 28. The AMF 28 is constructed with reference matter such as a replicate dielectric property matching material and is constructed to match the dipole field of the target material. The reference matter is analogous to the target material. The function and operation of the tension control spring 22, the pressure switch 24 and the accelerometer 20 are to provide output forces that may be used to quantify the DEP forces acting on the center beam 12.

Figure 2:
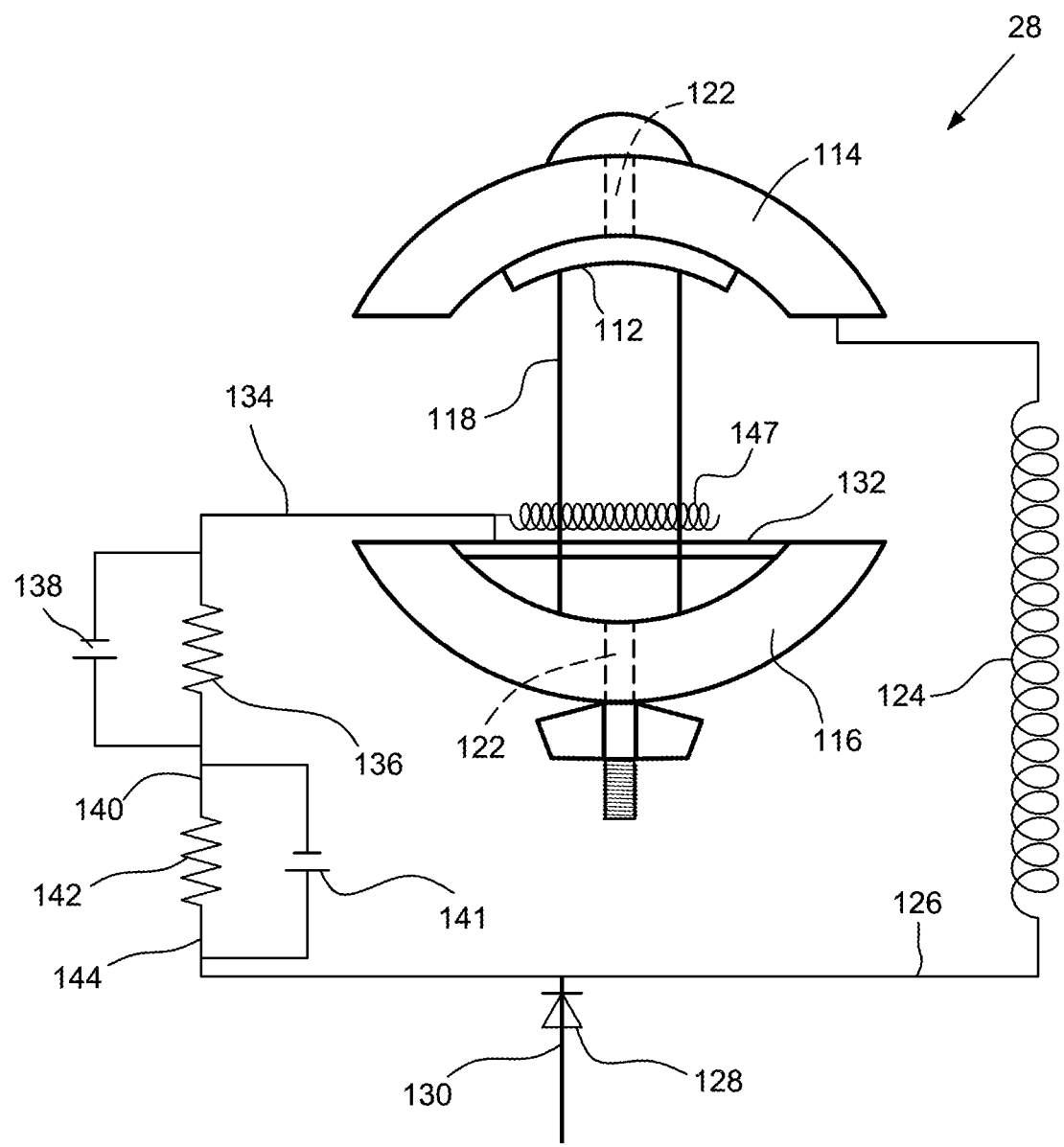
FIGS. 2 and 3 show an analog matching filter arrangement.
Figure 3:
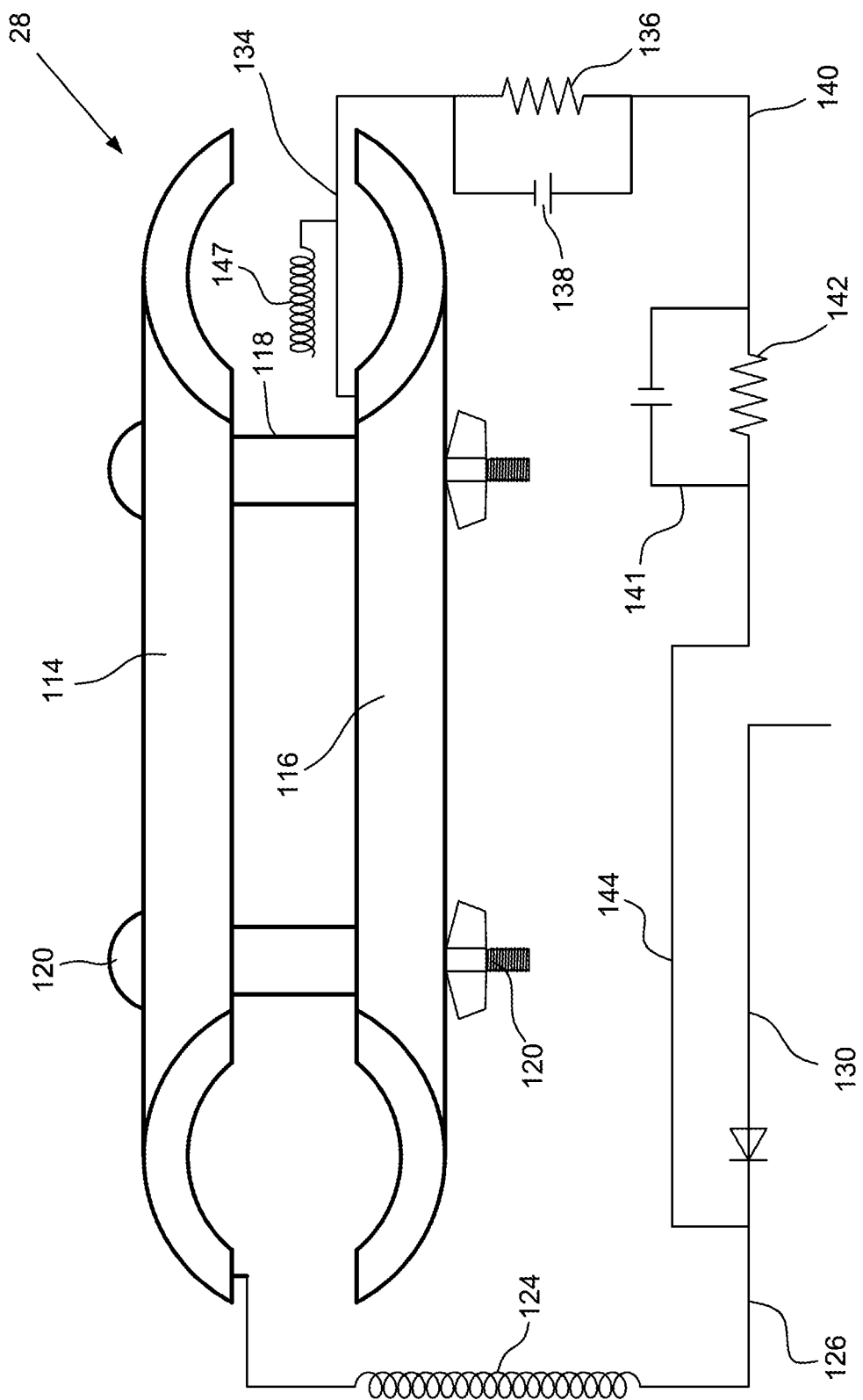

With reference to FIGS. 2 and 3, the analog matching polarization filter 28 is a composition of matter assembled so that the filter can perform; allowing the DEP to occur; resulting in a torque or resistance on the center beam 12 or the collector(s) 16 as it aligns with the spatial density of the non-uniform field. The application of electro, mechanical or magnetic sensors to the center beam 12 or collectors 19 enables the characterization and quantification of the DEP force acting on the center beam 12 or collectors 19. See FIGS. 6-8 for examples of the digitized output of center beam movement caused by the DEP force as it acts to align to the maxima of the spatial gradient of the electric field.

FIGS. 2 and 3 illustrate an exemplary filter 28. The filter 28 includes a replicate dielectric property matching material 112 within a spaced plate arrangement including a first plate 114 coupled with a second plate 116. In some embodiments, the replicate dielectric property matching material 112 is smokeless gunpowder. As shown, the plates 114, 116 may be curved along their longitudinal axes with concave surfaces facing each other. Alternatively, the plates 114, 116 may be parallel or constructed in different shapes. The pair of plates 114, 116 disposed enclosing the replicate dielectric property matching material 112 are held at a preferred distance by nylon spacers 118 secured via a suitable fastener 120. The plates 114, 116 may be formed by acrylonitrile-butadiene-styrene (ABS), for example, or other suitable polymers.

Each plate 114, 116 may be provided with a hole 122 at ends thereof or in each of the four corners of the plates. The plates 114, 116 are held at a set distance determined by the replicate material 112 by two to four of the spacers 118 through the holes 122. Each of the fastener 120 passes through one of the holes 122 in the plates 114, 116, through the spacer 118, through the opposing hole 122 in the opposite plate 114, 116, and a nut is applied to the threaded section of the fastener 120 to secure the plate 114, 116 and the spacers 118. The fastener 120 may be any suitable material such as stainless steel or nylon.

The replicate material 112 is disposed on an interior surface of the first plate 114 via an adhesive or the like such as cyanoacrylate. The amount of adhesive may be minimized so that the surface of the replicate material 112 is exposed and not encased by the adhesive. The replicate material 112 functionally performs a spatial dielectric property matching.

A copper wire or a silver coated copper wire 124 is connected to the first plate 114. The connection may be made in any suitable manner, and in an exemplary embodiment, the connection is made by drilling a hole in the cross section of the first plate 114 that is slightly larger than the diameter of the silver coated wire 124. An adhesive such as cyanoacrylate may be used to connect the first plate 114 at the drilled hole to the end of the silver-plated copper wire 124. The end of the silver coated silver wire 124 is inserted into the drilled hole in the first plate 114. The length of the wire 124 may be nominally two inches. The silver coated copper wire 124 when selected in the embodiment serves to reduce impedance.

A first conductive wire 126 connects the silver coated copper wire 124 to a diode 128. The connections are made by solder or the like. A second conductive wire 130 connects the diode 128 to an internal member 146 of a detector element (described below).

A copper plate or sheet 132 is attached to an interior surface of the second plate 116 by an adhesive, such as cyanoacrylate. A copper wire 147 is connected to the copper plate by solder. The copper wire increases the conductive surface area proximate to the replicate material. A third conductive wire 134 connects the copper plate 132 to a first resistor 136 and a first capacitor 138 in parallel. The connections may be made by solder or other suitable alternative. The first resistor 136 and the first capacitor 138 serve to produce a time constant less than 10 Hz.

A fourth conductive wire 140 connects the first resistor 136 and the first capacitor 138 to a second resistor 142 and a second capacitor 141 which are also in parallel. The connection may be made by solder or an alternative. The second resistor 142 and the second capacitor adjust the time constant less than 10 Hz.

A fifth conductive wire 144 connects the second resistor 142 in parallel with the capacitor 141 to the conductive wire 126 and then to the diode 128. The first plate 114 having the replicate material 112 attached is connected to the copper plate 132. The diode 128 is connected by the second conductive wire 130 to an internal member. The internal member reacts to currents in the conductive wires according to the principles of the described embodiments. The arrangement permittivity transmits (or "permits") an electric field to charge an analog matching filter, and allows electric field charge to be stored and converted to a DEP force. The selective permittivity is arranged in an analog matching filter in an RC circuit that enables the electric field stored charge to be converted to the DEP force, thereby enabling the detection of an entity, which is smokeless gunpowder according to the described embodiments.

The values of the resistors, capacitors and diodes are determined by the replicate material selected. That is, these values will vary for different replicate materials.

Acrylonitrile butadiene styrene (ABS) is currently used as plates defined as a mechanism for dynamic charging and electrostatic induction. Other materials may or may not be used for future configurations.

The charge/field separation of these plates are posts defined herein as nylon, a synthetic polymer or stainless steel but may or may not be another material utilized for the task of plate separation. Current creation utilizes two posts, but future configurations may include more or fewer posts of the same or different materials.

The material herein defined as analogous material is placed proximate to the conductive plate to match a material for detection using the transfer field and DEP.

The electrical components currently used for the analog matching filter are a capacitor and a metal film resistor where the value may or may not change depending on the material the sensor or detector is searching for.

A specific conductor acts as a drain for the analog matching filter.

Once the analog matching filter is connected to a circuit and a collector and center beam, DEP with resistance occurs with the changing of the electrons on the filter that will be measured via electro, mechanical or magnetic sensors.

The noted components are contained within an enclosure 30. The center beam 12 is fixed in the housing 30 relative to the collectors 16 to inhibit its movement and prohibit touching the enclosure 30. The enclosure 30 also includes detection indicator lights 32.

Figure 6:
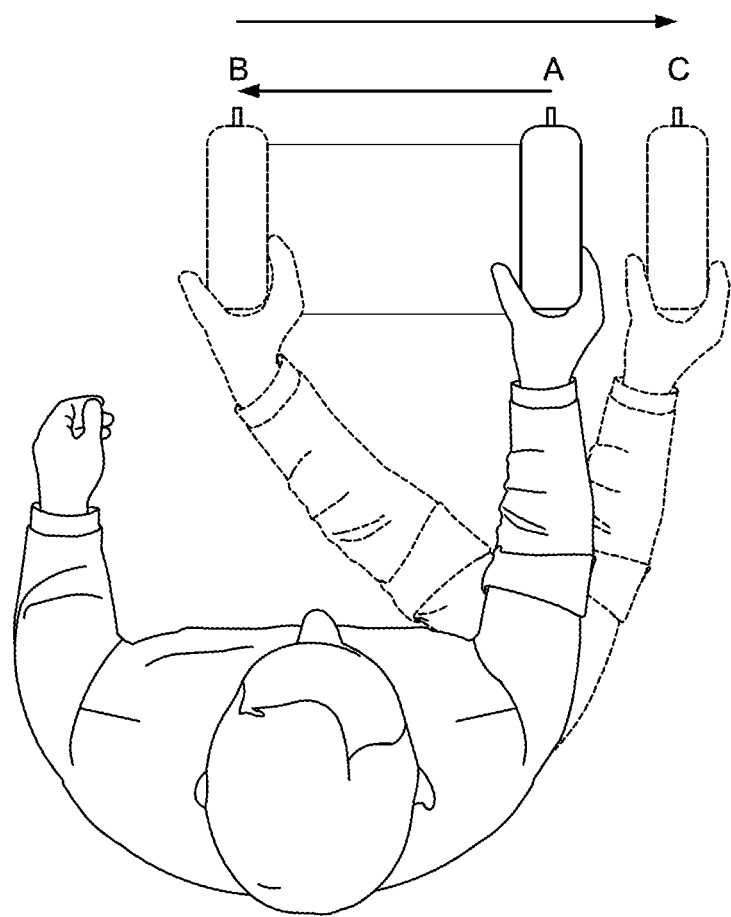
FIG. 6 shows a method of using the sensor device of the described embodiments to detect the presence of smokeless gunpowder.

With reference to FIG. 6, the remote detection of smokeless gunpowder is performed by the following steps. Smokeless gunpowder is present within the range of the detecting apparatus 10. The operator moves the detector 10 from point A to point B and immediately moves the detector 10 from point B to point C. The movement between points A-B and B-C may be performed with the detector 10 maintained in essentially a horizontal orientation. The movements themselves may also be performed in an essentially horizontal plane. The movement of the detector 10 passes thru the unique electric field spatial gradients. The selective permittivity in the detector's analog matching filter 28 in the RC circuit enables the unique electric field stored charge to be converted to the DEP force and enables the detection of the smokeless gunpowder. That is, the selective permittivity via the replicate matching material enables the opposite polarization pattern carried by the electrical circuit to be converted to the DEP force, thereby detecting the smokeless gunpowder.

Figure 7:
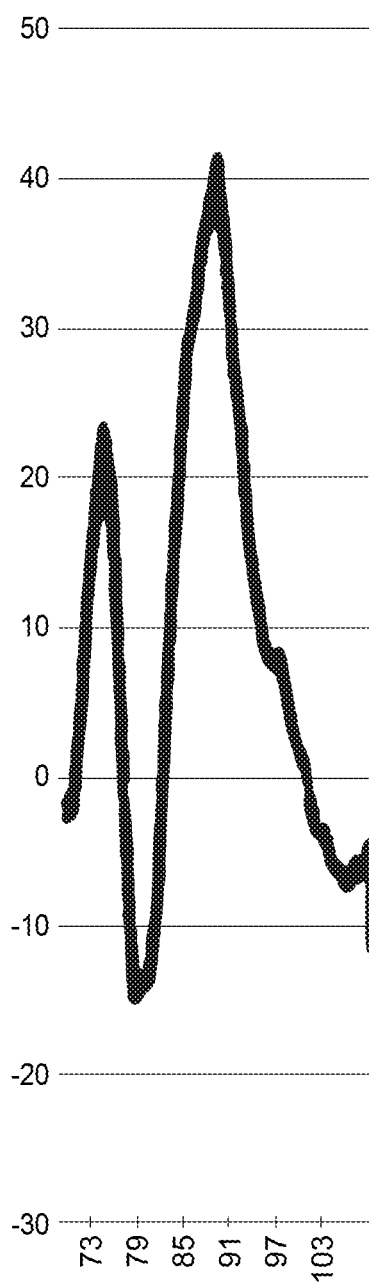
FIG. 7 is a graphic display of DEP force creating stress on the center beam.

When the device is scanned past a target material, stress is caused on the center beam 12, and a deflection of the center beam 12 caused by the DEP force is displayed as shown in FIG. 7. The stress on the center beam 12 is a product of the DEP force acting to align the center beam 12 to the highest spatial gradient of the target field. In FIG. 7, the X axis is time (approximately 1.5 seconds), and the Y axis is the amplitude of the DEP for on the center beam 12 (unitless value). The large impulse functions (Y axis) arises when the remote detector 10 passes through the maxima of the spatial gradient of the target's electric field.

Figure 8:
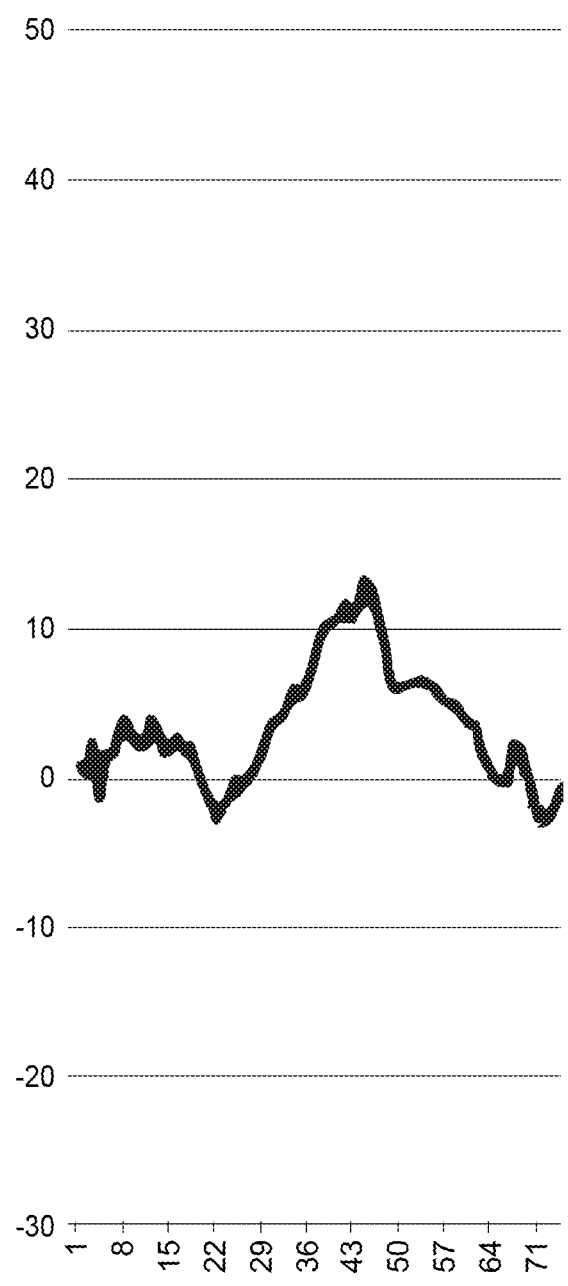
FIG. 8 is a graphic display showing acceleration and deceleration forces on the center beam caused by the operator scanning movements in FIG. 6.
Figure 9:
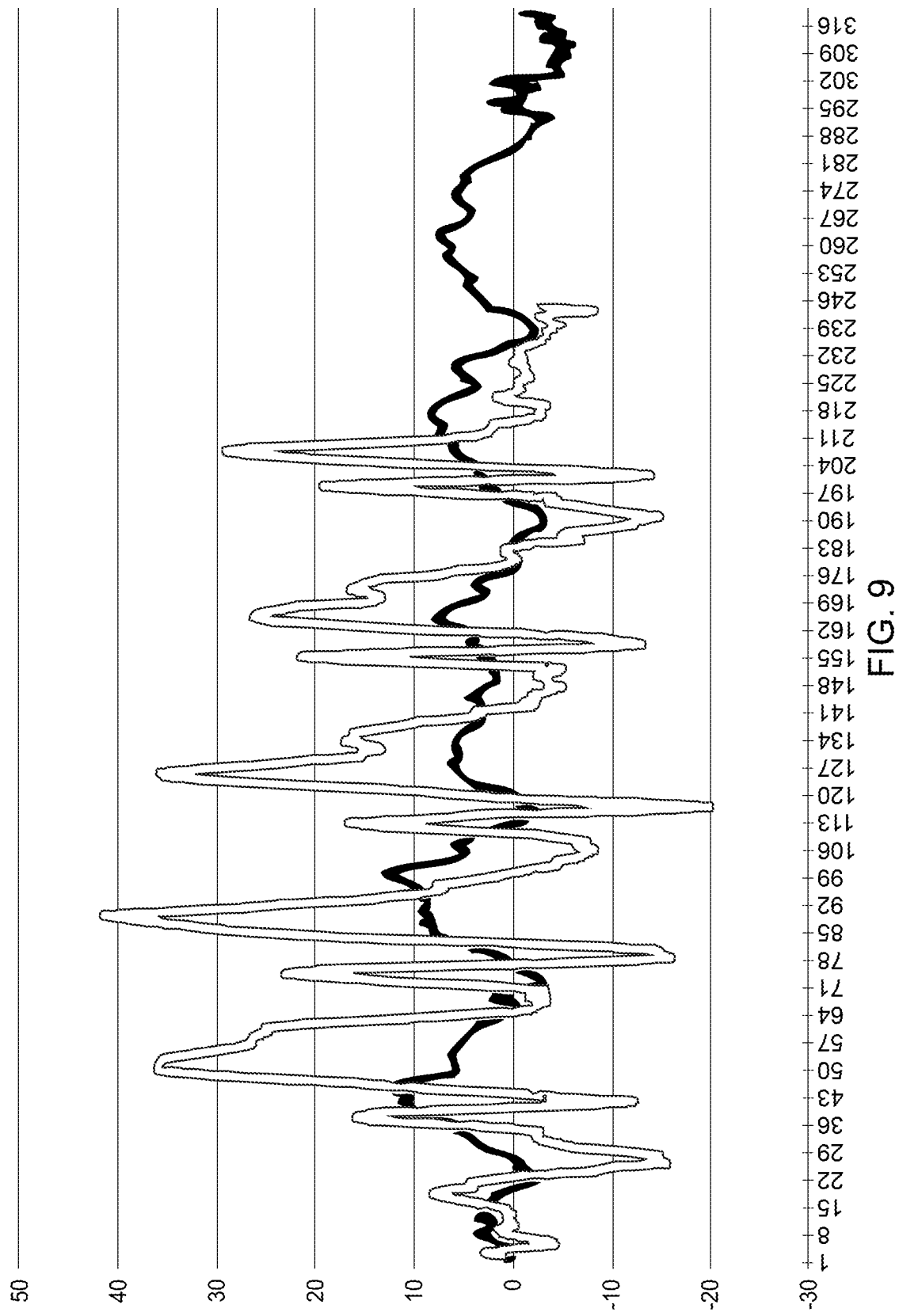
FIG. 9 is a graphic display of a comparative overlay of center beam forces when a target is present compared to a target not present.

When the remote detector 10 is scanned as in FIG. 6 and the target material is not present within the range of the remote detector 10, the forces on the center beam 12 are limited to the acceleration and deceleration forces produced by the mass of the center beam caused by the movements of FIG. 6, and the output is displayed as shown in FIG. 8. FIG. 9 is comparative overlay of center beam forces when a target is present compared to when a target not present. The presence of the targeted material may cause the center beam 12 to bend, which may be observed visibly, thereby displaying the DEP force. In some variations, the operator will not be able to observe the movement of the center beam 12. Rather, analog-to-digital sensor data will be displayed on the display to indicate the presence of the target material as shown in FIG. 7. Multiple analog-to-digital sensors and a processor will integrate and confirm the presence or no presence of the target material in the digital display.

With reference to FIG. 9, the DEP impulse functions produce a distinctive target present waveform (FIG. 7) as compared to the waveform when no target is present (FIG. 8). Analytical methods can be used to compare the waveform characteristics, to contrast center beam DEP forces to the remote detector enclosure movements indicated by the accelerometer and gyroscopic sensors.

Figure 10:
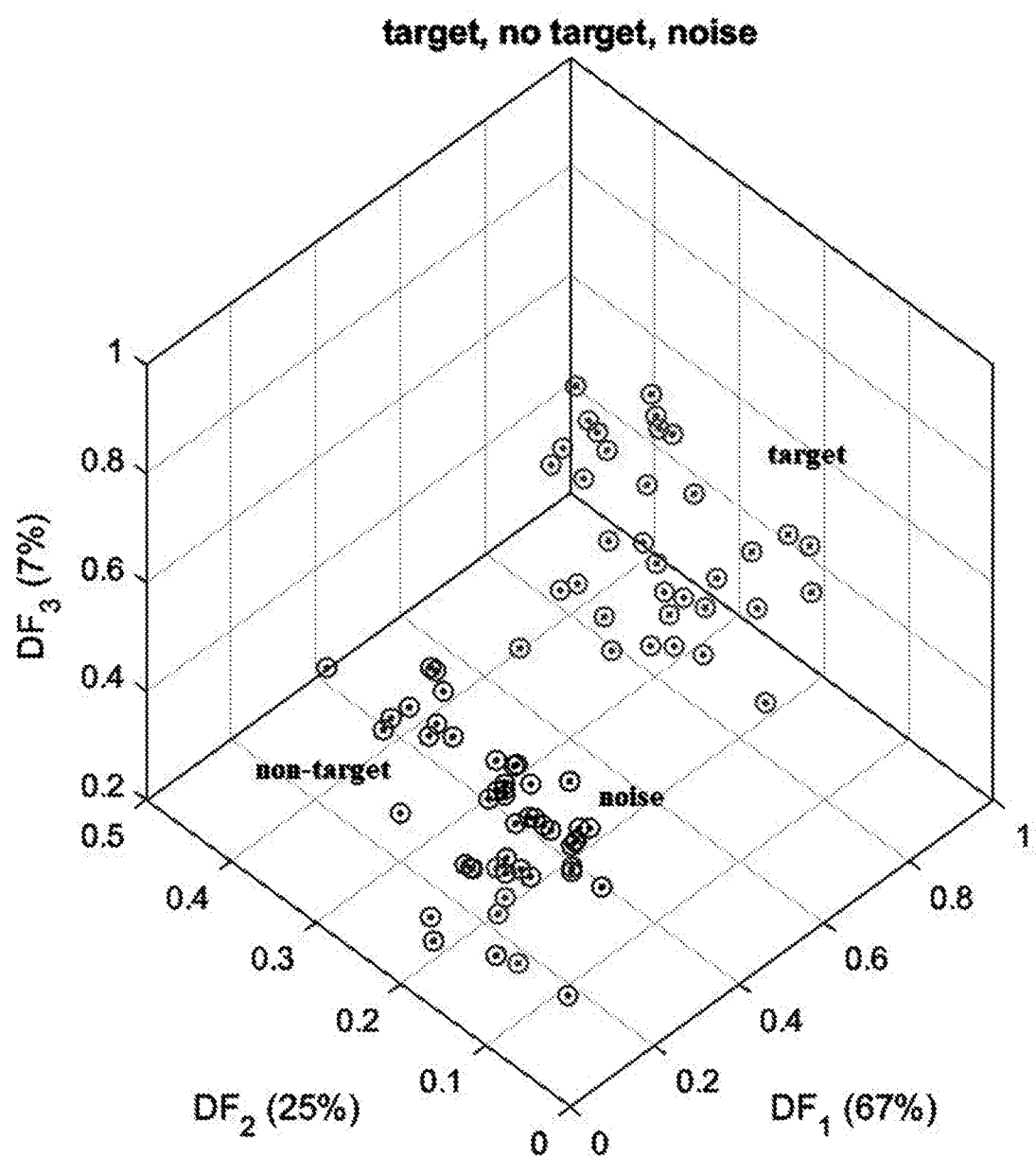
FIG. 10 shows an analytical analysis of multiple sensor inputs with classification of "Target" and "No Target."

The DEP force is quantified using multiple analytical techniques. The analytical techniques to quantify the force will be applied to the individual features of DEP. An example of a feature is acceleration of the center beam as the DEP force acts on the center beam to align with the target. Several analytical features will be correlated by processing software to confirm the DEP force. FIG. 10 is an example of weighted differential factors that enable sensitive classification of target present, non-target and noise. Quantification features include but are not limited to stress, acceleration, pressure, torque, current, voltage, and magnetic field changes. Analytical tools may be used to accurately classify the "target dielectric material present," "target dielectric material not present," and "remote detector system noise." One analytical method is to represent physical rates of changes using a differential equation such as $dy/dx=f(x)$. Several differential equations may be developed and weighted factors assigned to each differential equation to more accurately classify the operator scan.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A remote detector for detecting a presence of dielectric materials including energetic materials, the remote detector comprising:
   a center beam secured in a pivot mount;
   at least one collector secured to the center beam at a proximal end via the pivot mount; and
   an analog matching filter coupled with the center beam via a circuit, the analog matching filter including a replicate matching material configured to match a dipole field of a target material, the analog matching filter effecting a DEP force on the center beam.

2. A remote detector for detecting a presence of dielectric materials including energetic materials, the remote detector comprising:
   a center beam secured in a pivot mount;
   at least one collector secured to the center beam at a proximal end via the pivot mount; and
   an analog matching filter coupled with the center beam via a circuit, the analog matching filter including a replicate matching material configured to match a dipole field of a target material, wherein the analog matching filter comprises a selective permittivity that generates an opposite polarization pattern on the center beam via the circuit and thereby enables a unique electric field stored charge to be converted to a DEP force on the center beam.

3. A remote detector according to claim 1, comprising two collectors secured to opposite sides of the center beam.

4. A remote detector according to claim 3, wherein the collectors include a bend at a midpoint such that distal ends of the collectors are spaced from the center beam.

5. A remote detector according to claim 1, wherein the center beam is constructed of ABS plastic.

6. A remote detector according to claim 1, wherein the center beam is constructed of a combination of metal and dielectrics.

7. A remote detector according to claim 1, further comprising a displacement sensor positioned adjacent the collector.

8. A remote detector according to claim 7, wherein the displacement sensor comprises a contact terminal.

9. A remote detector according to claim 7, wherein the displacement sensor comprises a non-contact sensor.

10. A remote detector for detecting a presence of dielectric materials including energetic materials, the remote detector comprising:
- a center beam secured in a pivot mount;
- at least one collector secured to the center beam at a proximal end via the pivot mount;
- an analog matching filter coupled with the center beam via a circuit, the analog matching filter including a replicate matching material configured to match a dipole field of a target material; and
- a gyroscope accelerometer coupled with the center beam and connected to the circuit.

11. A remote detector according to claim 1, further comprising a housing containing the center beam, the collector and the analog matching filter.

12. A remote detector according to claim 1, further comprising detection indicator lights coupled with the circuit, the circuit illuminating the detection indicator lights when displacement of the center beam is detected.

* * * * *